US007682844B2

(12) United States Patent
Naoe et al.

(10) Patent No.: US 7,682,844 B2
(45) Date of Patent: Mar. 23, 2010

(54) SILICON SUBSTRATE PROCESSING METHOD FOR OBSERVING DEFECTS IN SEMICONDUCTOR DEVICES AND DEFECT-DETECTING METHOD

(75) Inventors: Takuya Naoe, Osaka (JP); Hirohiko Endoh, Osaka (JP)

(73) Assignee: Ricoh Company, Ltd., Tokyo (JP)

( * ) Notice: Subject to any disclaimer, the term of this patent is extended or adjusted under 35 U.S.C. 154(b) by 387 days.

(21) Appl. No.: 11/431,743

(22) Filed: May 10, 2006

(65) Prior Publication Data
US 2006/0264005 A1 Nov. 23, 2006

(30) Foreign Application Priority Data
May 11, 2005 (JP) ............................. 2005-138161
May 12, 2005 (JP) ............................. 2005-139518

(51) Int. Cl.
*H01L 21/66* (2006.01)
(52) U.S. Cl. ................. 438/16; 438/7; 438/10; 438/17; 257/E21.527; 257/E21.528
(58) Field of Classification Search ............ 438/14–18, 438/460, 690, 692, 800, FOR. 101, FOR. 102, 438/7, 10; 257/E21.521, E21.525, E21.527, 257/E21.528; 250/559.27, 559.28, 559.4
See application file for complete search history.

(56) References Cited
U.S. PATENT DOCUMENTS 5,334,540 A * 8/1994 Ishii ............................. 324/765
5,540,810 A * 7/1996 Sandhu et al. ............... 438/693
5,804,980 A * 9/1998 Nikawa ........................ 324/752
5,814,885 A * 9/1998 Pogge et al. ................. 257/730
6,069,366 A * 5/2000 Goruganthu et al. ... 250/559.27
6,406,924 B1 * 6/2002 Grimbergen et al. ........... 438/9
6,955,930 B2 * 10/2005 Le Roy et al. ................. 438/16
2003/0113941 A1* 6/2003 Naruoka ....................... 438/14
2004/0087146 A1* 5/2004 Paterson et al. ............. 438/687
2006/0138323 A1* 6/2006 Chang et al. ................ 250/307
2006/0188797 A1* 8/2006 Roy et al. ...................... 430/30

FOREIGN PATENT DOCUMENTS

| JP | 9-199069 | 7/1997 |
| JP | 2001-217290 | 8/2001 |
| JP | 3485707 | 1/2004 |
| JP | 2004-228076 | 8/2004 |

* cited by examiner

*Primary Examiner*—Matthew Smith
*Assistant Examiner*—Quovaunda Jefferson
(74) *Attorney, Agent, or Firm*—Cooper & Dunham, LLP

(57) ABSTRACT

A silicon substrate processing method for reducing the thickness of an area of a silicon substrate on which a metal layer is formed to implement a semiconductor integrated circuit is disclosed. The method includes: (A) a process which evenly reduces the thickness of the backside of a silicon substrate to an extent where mechanical strength is maintained and the metal layer on the silicon substrate remains intact; (B) a process which detects defects from the backside of the silicon substrate after the process (A); (C) a process which further reduces the thickness of a defect-containing area of the silicon substrate by processing the backside of the silicon substrate; and (D) a process which measures the thickness of the area of the silicon substrate which is reduced in the process (C).

19 Claims, 16 Drawing Sheets

SILICON SUBSTRATE PROCESSING METHOD FOR OBSERVING DEFECTS IN SEMICONDUCTOR DEVICES AND DEFECT-DETECTING METHOD

BACKGROUND OF THE INVENTION

1. Field of the Invention

The present invention generally relates to a silicon substrate processing method for the observation of defects in semiconductor devices and a defect-detecting method.

2. Description of the Related Art

When a VLSI silicon device having a semiconductor integrated circuit formed on a silicon substrate fails, it is required to detect the defects causing the failure and examine the nature of those defects.

To observe defects, a transmission electron microscope (TEM) may be used. For the TEM observation, preparation of a very thin sample through which an electron beam can penetrate is required. For example, for the TEM observation using an electron beam with an accelerating voltage of 200 kV, the thickness of the sample to be observed should be around 0.1 µm. Some methods using a focused ion beam (FIB) to cut out a defect-containing area have been proposed for the preparation of samples used for the TEM observation (Patent documents 1 through 3).

Before preparing such a very thin sample, it is necessary to identify the specific location of a defect in the silicon substrate or the metal layer formed on the front side of the substrate. The present invention relates to a method for identifying specific locations of defects.

Known defect-detecting techniques include the optical beam induced current (OBIC) technique, the optical beam induced resistance change (OBIRCH) technique, and the photoemission microscopy (PEMS) technique.

In the OBIC and OBIRCH techniques, a constant voltage is applied to a target device, the observation point in the device is scanned and irradiated with a laser beam, and each electric current variation is displayed as a brightness signal variation on a point on the screen which corresponds to each point in the scanned area. The OBIC technique uses a visible laser (with a wavelength of 623.8 nm, for example) to detect electric current variations in a silicon substrate. The OBIRCH technique uses a visible laser (with a wavelength of 623.8 nm, for example) or a near-infrared laser (with a wavelength of 1300 nm) to detect resistance variations in a metal layer which are caused by temperature rise.

The PEMS technique uses luminescence which is seen when a voltage is applied to a target device. If the device has a defect such as junction leakage or a damaged insulator film, the electric field is concentrated near the defect and hot carriers are generated. The hot carriers emit light when they recombine. The PEMS technique detects this light to identify the location of the defect.

Detection of defects may be performed either from the front side or the backside of a silicon device. However, in defect detection from the front side, emission leakage through the metal layer may prevent accurate detection of defects. In defect detection from the backside, the surface pattern is recognized through infrared ray observation, the surface pattern is scanned (using CAD navigation, for example), and the area to be processed is determined. Also, to open the front side of the device, the backside opening should be closed to maintain the mechanical strength of the sample. Therefore, after opening the front side, it is difficult to electrically detect defects from the backside.

In defect detection from the backside, if the thickness of the silicon substrate is 15 µm or more, the resolution and the location accuracy become low. Furthermore, even if a defect is detected, the thicker the silicon substrate, the longer it takes to cut out a sample from the backside for the TEM observation.

[Patent document 1] Japanese Patent No. 3485707
[Patent document 2] Japanese Patent Application Publication No. 2001-217290
[Patent document 3] Japanese Patent Application Publication No. 2004-228076

To detect defects from the backside of a silicon substrate and to improve the accuracy of location identification, it is necessary to create a thin silicon substrate.

A thinner silicon substrate is better for highly-accurate detection of defects. Normally, diffusion layers are formed on the front side of a silicon substrate, for which a well is deeper than other types of diffusion layers and has a depth of 1.5 to 2.0 µm. Since defects in a substrate are normally found in the diffusion layers, it is not appropriate to make a silicon substrate thinner than the depth of diffusion layers. Consequently, the most suitable thickness of a silicon substrate when detecting defects is 2 to 5 µm.

One way to reduce the thickness of the backside of a silicon substrate is to evenly grind the entire area. However, if the entire silicon substrate is very thin, less than 10 µm for example, the mechanical strength of the substrate becomes low and handling of the substrate becomes very difficult.

Another way is to reduce the thickness of a defect-containing area only. For this partial processing, a laser beam or a FIB may be used. In this method, the remaining thickness of the defect-containing area should be measured. Since the infrared ray can penetrate a silicon substrate, the thickness can be measured by focusing an infrared microscope on the front side and backside of the processed silicon substrate. However, the accuracy of this method is low and it is difficult to precisely measure a very thin silicon substrate with a thickness less than 10 µm.

SUMMARY OF THE INVENTION

The present invention may provide a silicon substrate processing method for observing defects in semiconductor devices and a defect-detecting method that substantially obviate one or more problems caused by the limitations and disadvantages of the related art.

A preferred embodiment of the present invention may particularly provide a method for accurately reducing the thickness of an area of the backside of a silicon substrate on which a semiconductor integrated circuit is formed, and a method for accurately detecting defects.

To achieve these and other advantages in accordance with an aspect of the present invention, a silicon substrate processing method which reduces the thickness of an area of a silicon substrate on which a metal layer is formed to implement a semiconductor integrated circuit includes: (A) a process which evenly reduces the thickness of the backside of a silicon substrate to an extent where mechanical strength is maintained and the metal layer on the silicon substrate remains intact; (B) a process which detects defects from the backside of the silicon substrate after the process (A); (C) a process which further reduces the thickness of a defect-containing area of the silicon substrate by processing the backside of the silicon substrate; (D) a process which measures the thickness of the area of the silicon substrate which is reduced in the process (C), including at least a step that measures the thickness based on interference fringes formed by irradiating the substrate from the backside with a light.

In the silicon substrate processing method according to an embodiment of the present invention, only the thickness of a defect-containing area is reduced from the backside of a silicon substrate. Therefore, even if the thickness of the defect-containing area is less than 10 μm, 2 to 5 μm for example, the mechanical strength of the entire silicon substrate can be maintained and an electrical defect-detecting technique can be used for the silicon substrate.

Also, since the silicon substrate processing method includes a process which measures the thickness of the defect-containing area of a silicon substrate based on the formation of interference fringes, the thickness measurement of a silicon substrate is highly reproducible, and the thickness of a desired point in the observation area can be measured.

Further, since the backside of a silicon substrate is processed with the metal layer left intact, techniques, such as the OBIC technique, the OBIRCH technique, and the PEMS technique, which incorporate detection of electrical characteristics, can be used. Also, since the defect-containing area used to detect defects is very thin, the influence of the silicon substrate and the metal layer on the front side is small and the accuracy of defect-location identification is high.

In an embodiment of the present invention, the location of a defect is marked on the backside of the silicon substrate. This marking eliminates the need for alignment with the pattern on the front side when cutting out a sample for the TEM observation. Since the mark is placed on the backside of a silicon substrate, a laser in an apparatus for processing the silicon substrate can be used for this marking. Also, marking on the backside of a silicon substrate has an advantage over a method in which the location of a defect is marked on the front side, since the latter method needs to use a technique such as FIB deposition because of the presence of the pattern on the front side.

In addition, since the detection of electrical characteristics is possible, the accuracy of defect-location identification can be improved further by correcting the position of the mark after the first marking.

If both the etching step using a laser beam and the subsequent anisotropic wet etching step using an alkaline solution are incorporated in the thickness-reducing process, the anisotropic wet etching step is simplified because there is no need to form an anti-etching mask. Also, since an alkaline solution does not cause much damage to the metal layer or the molding compound on the front side of a silicon substrate, detection of electrical characteristics is possible even after the wet etching step. Damage on the front side metal layer can be prevented further by using a laser beam, particularly a short-wavelength laser beam for which an absorption coefficient of silicon is large, to process the silicon substrate.

Interference fringes do not appear in the defect-containing area of a silicon substrate until the thickness becomes less than 10 μm. Until then, an infrared ray can be used to measure the thickness of the defect-containing area of the silicon substrate.

The range of the thickness which can be measured based on interference fringes in the defect-containing area of the silicon substrate depends on the wavelength and intensity of a light. Use of a laser beam provides a light with a precise wavelength and improves the accuracy of the measurement.

Use of two laser beams with different wavelengths further improves the accuracy of measuring the thickness of the defect-containing area of the silicon substrate.

Combining the interference fringe observation and the pattern observation using a scanning electron microscope (SEM) improves the accuracy of measuring the thickness of the defect-containing area of the silicon substrate even more.

A desired thickness of the defect-containing area of the silicon substrate can be easily achieved by alternately repeating the anisotropic wet etching and the thickness measurement until interference fringes appear, and even until the pattern on the front side can be observed by using a SEM; or by continuing the anisotropic wet etching for a specific period of time after the interference fringes appear.

A defect-detecting method according to the present invention includes a process which processes a silicon substrate to achieve a thickness that enables appearance of light interference fringes, is greater than a depth of diffusion layers formed on the front side of the silicon substrate, and allows a visible laser beam to reach the diffusion layers from the backside of the silicon substrate; and a subsequent process which identifies locations of defects. With this method, the locations of defects such as a PN junction leakage and a gate oxide leakage can be selectively identified.

In this defect-detecting method, if no defect is detected, locations of defects in a metal layer formed on the front side of the silicon substrate can be identified by performing anisotropic wet etching until no silicon substrate is left in the defect-containing area.

The present invention improves the efficiency of the entire process by performing all defect-detecting processes consecutively using a single apparatus, in which the OBIC technique is used to detect defects in a silicon substrate, the OBIRCH technique is used to detect defects in a metal layer, and a visible laser beam is used in both techniques.

DETAILED DESCRIPTION OF THE PREFERRED EMBODIMENTS

In the following, embodiments of the present invention are described in detail with reference to accompanying drawings.

FIGS. 1A through 1D are cross-sectional drawings outlining the processes according to the present invention.

Figure 1A:
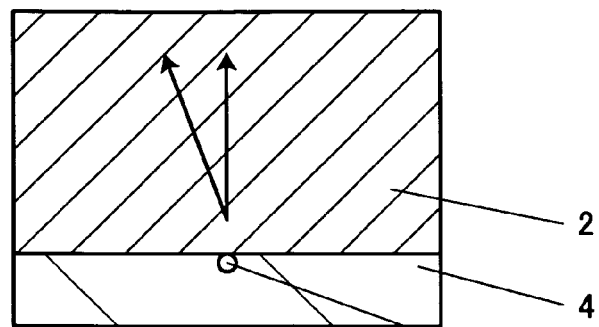
FIGS. 1A through 1D are cross-sectional drawings outlining the processes according to the present invention.

In FIG. 1A, the backside of a silicon substrate 2 of a failed semiconductor integrated circuit device is ground until the thickness of the silicon substrate 2 becomes around 100 μm. The side on which a metal layer 4 is formed is called the pattern side or the front side, and the other side is called the backside. The thickness of the silicon substrate 2 is controlled by the grinding time. The thickness is measured, by using an infrared microscope, based on either a distance between focal points obtained by focusing the infrared microscope on the front side and backside of the silicon substrate 2, or an infrared ray intensity where the ray penetrates through the silicon substrate 2. When the thickness of the silicon substrate 2 is around 100 μm, the mechanical strength can be maintained.

Next, a defect 6 is detected using the OBIC technique, the OBIRCH technique, or the PEMS technique. Although the defect 6 is shown in the metal layer 4 in the drawings, a defect may be found in the silicon substrate 2.

After the defect 6 is identified, the location of the defect 6 is marked on the backside. For this marking, a laser beam may be used. The mark is placed directly above the defect 6.

Figure 1B:
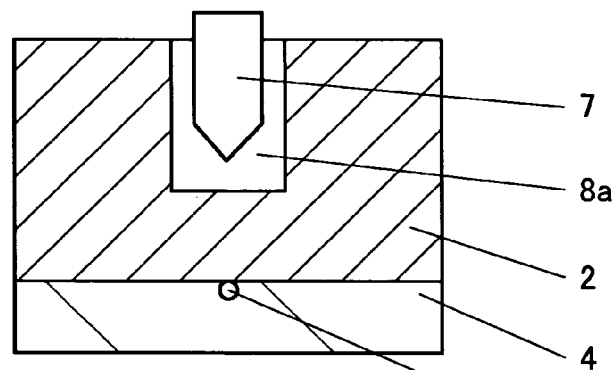

In FIG. 1B, the area containing the defect 6 is etched from the backside of the silicon substrate 2 using a laser beam 7 to form a concave area. A hole 8a is formed by the above process. The suitable depth of the hole 8a is around 70 μm.

Figure 1C:
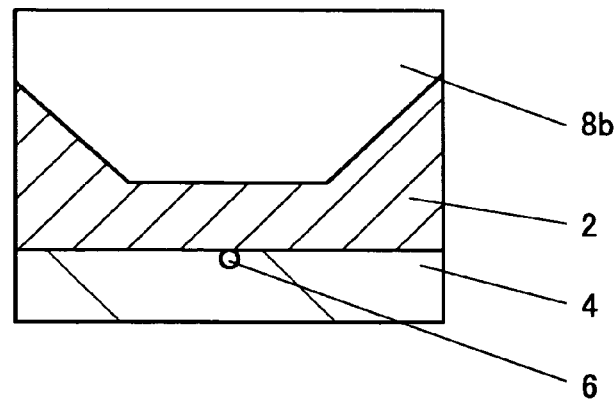

In FIG. 1C, the entire substrate is dipped in a KOH or TMAH solution to perform anisotropic wet etching. In this wet etching using an alkaline solution, etching proceeds through the hole 8a. Therefore, no anti-etching mask is required. Also, if the silicon substrate has a (100) plane, etching proceeds in the oblique direction and forms an opening 8b which gradually widens toward the backside.

Wet etching is controlled by the etching time. The wet etching is performed until interference fringes can be formed in the defect-containing area of the silicon substrate 2 by irradiating the area with a laser beam. If a He—Ne laser or a near-infrared laser is used for this purpose, interference fringes appear when the thickness of the defect-containing area of the silicon substrate is 10 μm or less. The thickness at which interference fringes appear depends on the wavelength of a light used. The wet etching and the observation for interference fringes are repeated alternately until interference fringes appear.

Even after the interference fringes appear, the wet etching may be continued for a specific period of time to reduce the thickness of the silicon substrate area further. Since the wet etching rate can be accurately calculated by specifying conditions, the thickness of the silicon substrate area can be controlled by the etching time.

At this stage, the location of the defect 6 is identified again by using the OBIC technique, the OBIRCH technique, or the PEMS technique. Although the location of the defect 6 is already identified in the process shown in FIG. 1A, more accurate identification is possible in the process shown in FIG. 1C, since the defect-containing area of the silicon substrate 2 is much thinner now. Then, the location of the defect 6 is marked. For this marking, a laser beam may be used. The mark is placed on the backside of the silicon substrate 2 and consists of four points on the left, right, top, and bottom of the defect 6. The defect 6 comes in the center of the four points. After the location is marked, the location of the defect 6 is identified once again by using the OBIC technique, the OBIRCH technique, or the PEMS technique. If the newly identified location of the defect 6 is not in the center of the four points, the position of the mark is corrected so that the location of the defect 6 is in the center of the four points.

The defect 6 detected in the process shown in FIG. 1C will always be in the silicon substrate. When the thickness of the defect-containing area of the silicon substrate is 2 to 5 μm, a visible laser used for detecting defects reaches the diffusion layers but not the metal layer. Therefore, a defect detected in this process will always be in the silicon substrate.

If no defect is detected in the process shown in FIG. 1C, it means that there is no defect in the silicon substrate. Therefore, in the process shown in FIG. 1D, wet etching is continued until no silicon substrate remains in the defect-containing area of the silicon substrate 2. An oxide film formed on the upper surface of the silicon substrate 2 works as an etching-stopper layer, and the wet etching stops automatically when the oxide film is exposed. An opening 8c shows the shape of the opening when the wet etching is continued until the oxide film of the defect-containing area of the silicon substrate 2 is exposed.

Figure 1D:
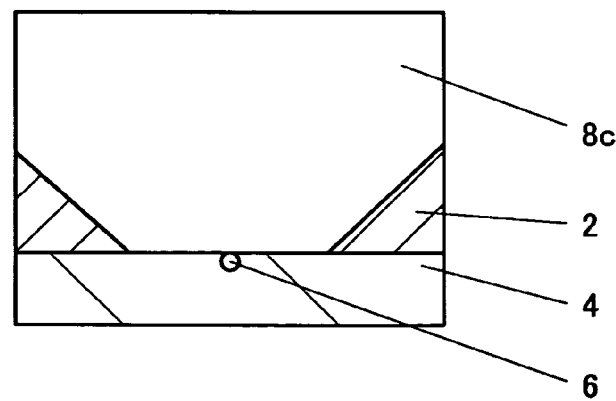

Even at the stage shown in FIG. 1D, since the opening 8c is only a limited area of the silicon substrate 2 and the remaining area has a thickness of around 100 μm, the mechanical strength of the silicon substrate 2 is still maintained. Also, since the metal layer is left intact, defect detection can be performed again on the metal layer by using the OBIC technique, the OBIRCH technique, or the PEMS technique.

In the method according to the present invention, the defect 6 is detected and its location is identified in the processes shown in FIG. 1C and FIG. 1D. After these processes, a sample for the TEM observation can be created from the processed silicon substrate 2 by cutting out the defect-containing area by using a FIB. For cutting out a sample, a micro sampling method using a FIB described in the patent documents 2 or 3 may be used. Another method for cutting out a sample is also described below.

In the following, preferred embodiments are described in more detail.

1. First Embodiment

In process 1-1, the backside of a silicon substrate is ground.

Figure 2:
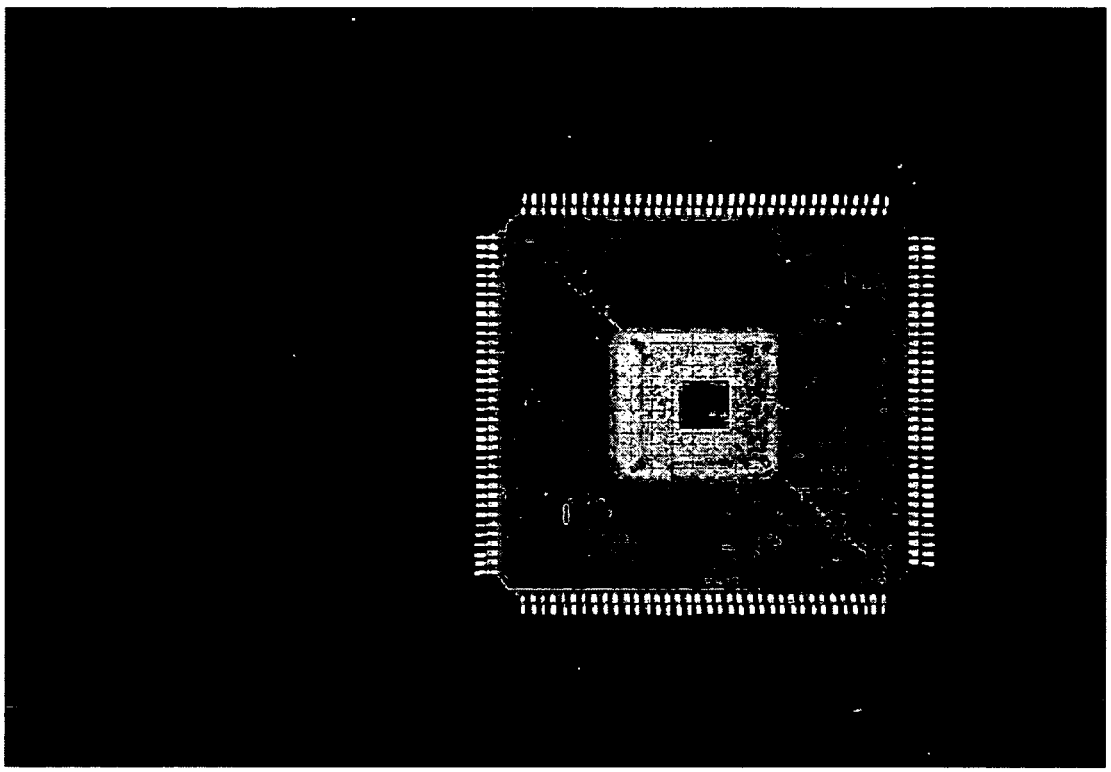
FIG. 2 is an image in a first embodiment of the exposed backside surface of a silicon substrate chip of a failed semiconductor integrated circuit device.

FIG. 2 is an image of the exposed backside surface of a silicon substrate chip of a failed semiconductor integrated circuit device. The metal layer on the front side of the device is left intact so that the device is electrically operable. The exposed backside of the silicon substrate is evenly ground until the entire thickness of the silicon substrate 2 becomes around 150 µm.

In process 1-2, defect detection is performed.

Figure 3A:
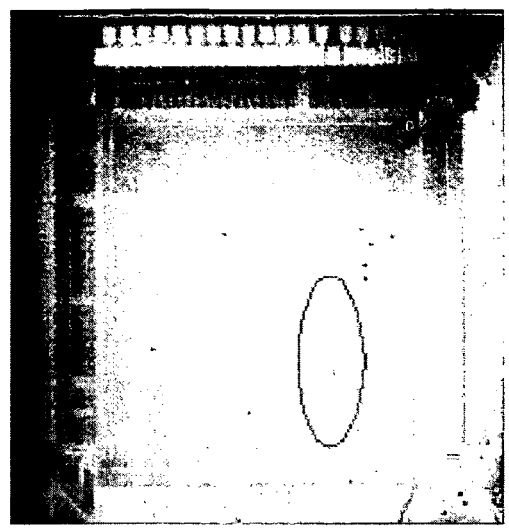
FIGS. 3A through 3C are images showing the pattern on the front side which is observed from the backside using an infrared microscope at (3A) 5-, (3B) 20-, or (3C) 100-fold magnification, respectively.
Figure 3B:
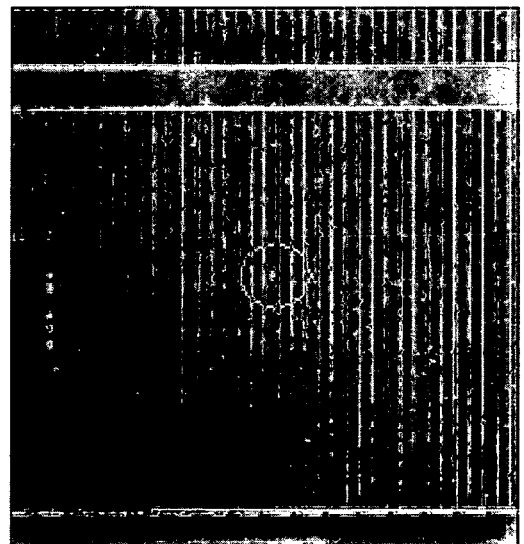
Figure 3C:
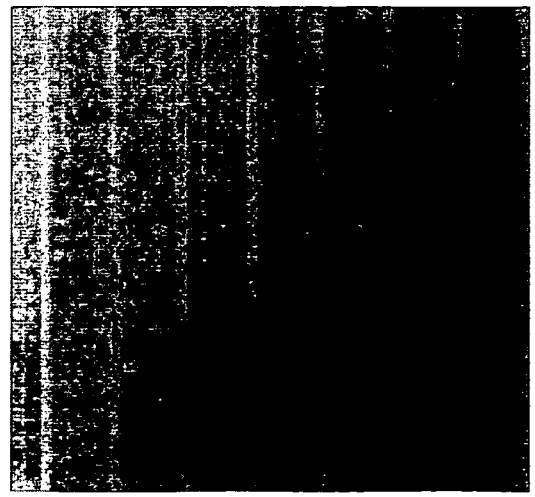

FIGS. 3A through 3C are images showing the pattern on the front side which is observed from the backside using an infrared microscope at (3A) 5-, (3B) 20-, or (3C) 100-fold magnification, respectively.

The PEMS technique or the OBIRCH technique is used to detect defects and to identify their locations. In this embodiment, the PEMS technique is employed, in which a voltage of 3.0 V is applied to the substrate and a laser beam is used to irradiate the defect. In each of FIGS. 3A through 3C, the circled area shows the location of the defect.

The location of the defect is then marked on the backside of the silicon substrate by using a laser beam.

Figure 4A:
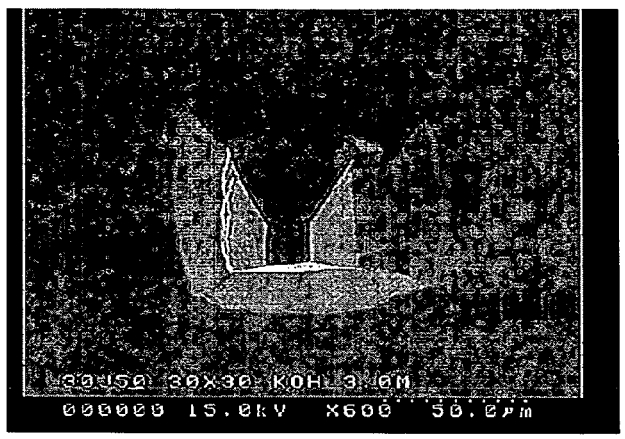
FIG. 4A is an image showing the defect-containing area.

In process 1-3, only the thickness of the area containing the defect is reduced. To reduce the thickness, as shown in FIG. 4A, the backside of the defect-containing area is processed using a short-wavelength laser beam to form a concave area, and then processed by wet etching using an alkaline solution. The wet etching selectively dissolves the area processed with the laser beam.

For the laser processing, a laser in the PEMS apparatus or a laser in another apparatus may be used. When a laser in another apparatus is used, the same coordinate system should be used in both the PEMS apparatus and the other apparatus to determine the area to be processed. A short-wavelength laser beam with a wavelength of 248 nm and a fluence of 25 J/cm$^2$ is used in this embodiment. The size of the opening of the hole is 60 µm×60 µm. A short-wavelength laser beam is easily absorbed by the silicon substrate and does not damage the front side pattern.

The wet etching is performed using a TMAH or KOH solution as the alkaline solution for around 40 minutes at a temperature of 85° C. The wet etching proceeds in an oblique direction and the center of the silicon substrate becomes thinnest. Also in this wet etching process using an alkaline solution, the front side pattern is not damaged.

Figure 4B:
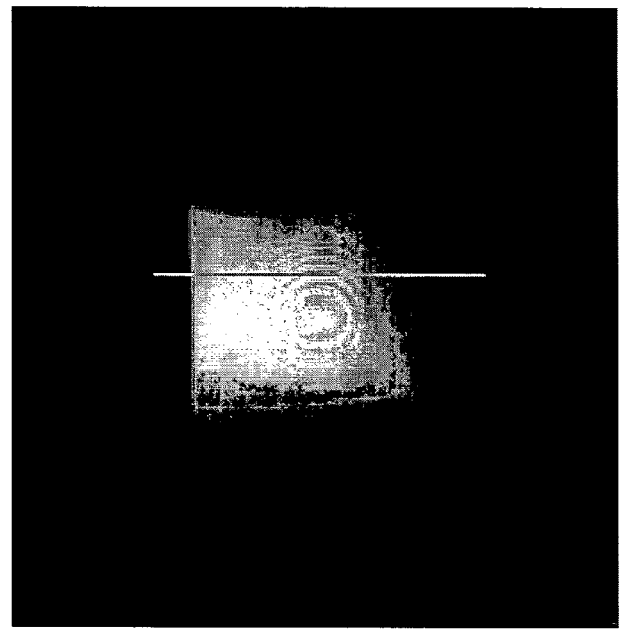
FIG. 4B is an image showing interference fringes formed by a He—Ne laser.
Figure 4C:
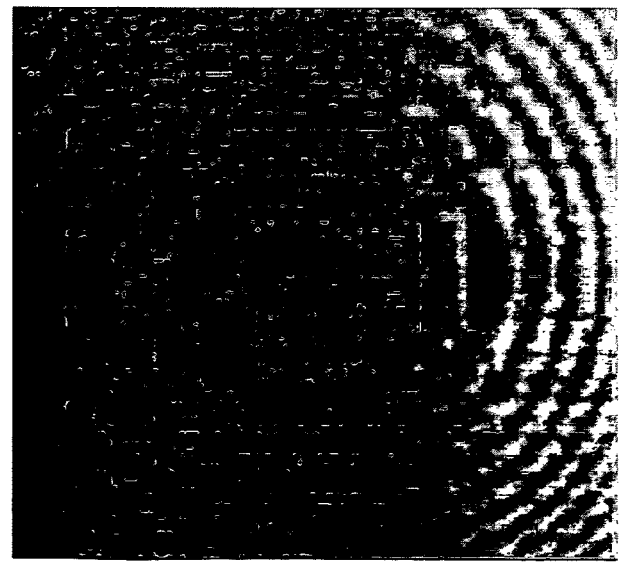
FIG. 4C is an image showing interference fringes formed by an infrared ray.

The remaining thickness of the defect-containing area of the silicon substrate is measured based on interference fringes formed by using a He—Ne laser (with a wavelength of 632.8 nm) as shown in FIG. 4B or by using an infrared camera (with a wavelength of 1100 nm) as shown in FIG. 4C. The wet etching on the silicon substrate and observation for interference fringes are repeated alternately until interference fringes appear. The etching rate is approximately 1.5 to 2.0 µm/minute.

Figure 5:
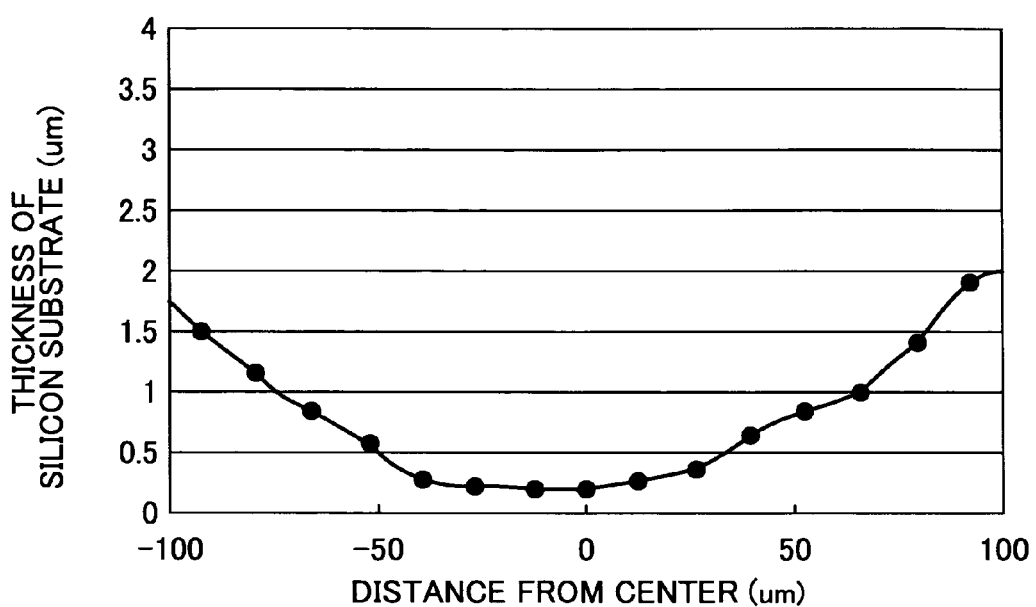
FIG. 5 is a graph showing the remaining thickness of the defect-containing area of a silicon substrate.

FIG. 5 is a graph showing the remaining thickness of the defect-containing area of a silicon substrate. The graph shows the thicknesses at plural points in the defect-containing area which are measured when the thickness of the center of the area is reduced to around 0.2 µm by the wet etching process. The graph also shows that the wet etching proceeds so that the center of the area is thinnest and the thickness gradually increases in oblique direction toward both edges. When the shape as shown in FIG. 5 is achieved, interference fringes appear.

Figure 6:
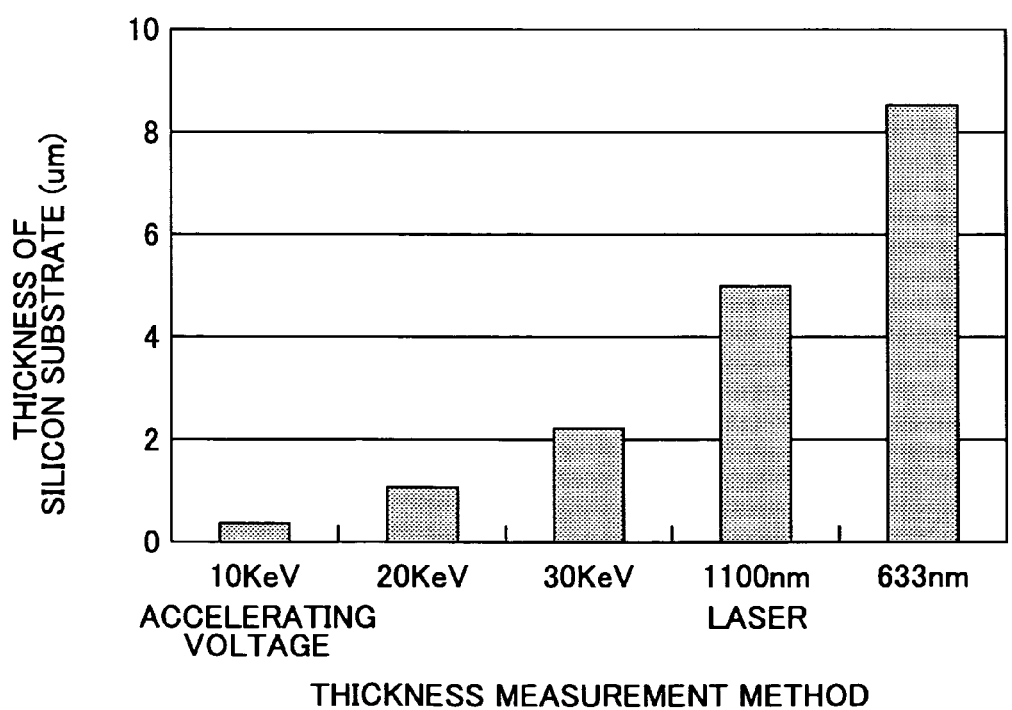
FIG. 6 is a graph showing the range of thickness of a silicon substrate which can be measured based on the results of thickness measurements using light interference fringes or the results of pattern observation using a SEM at several accelerating voltages.

FIG. 6 is a graph showing the range of thickness of a silicon substrate which can be measured based on the results of thickness measurements using light interference fringes and the results of pattern observation using a SEM at several accelerating voltages.

In observation using a He—Ne laser beam with a wavelength of 632.8 nm, interference fringes appear when the thickness of the defect-containing area of the silicon substrate is 8.5 µm or less. In observation using an infrared ray with a wavelength of 1100 nm, interference fringes appear when the thickness of the defect-containing area is 4.5 µm or less. If interference fringes are formed by using the 632.8 nm wavelength laser beam and not formed by using the 1100 nm wavelength infrared ray, the thickness is measured to be in the range of 4.5 to 8.5 µm.

In observation using a SEM at an accelerating voltage of 20 keV, the front side pattern can be observed through a silicon substrate with a thickness of 2.2 µm. As the accelerating voltage decreases, the thickness of the substrate through which an electron can penetrate decreases.

By using both the interference fringe observation and the SEM observation, the silicon substrate thickness of less than 10 µm can be measured. For example, if interference fringes are formed by using the 1100 nm wavelength infrared ray and if the front side pattern cannot be observed by using a SEM at an accelerating voltage of 30 keV, the thickness is measured to be in the range of 2.2 to 4.5 µm.

Figure 7A:
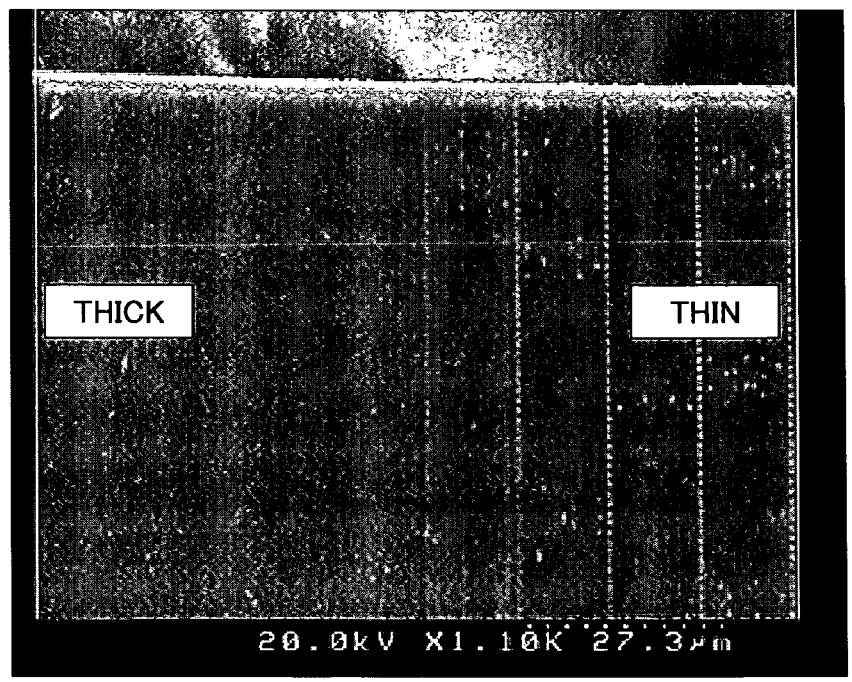
FIGS. 7A and 7B are images showing the pattern on the front side observed by using a SEM at the accelerating voltage of 20 keV (7A) or 30 keV (7B) respectively.
Figure 7B:
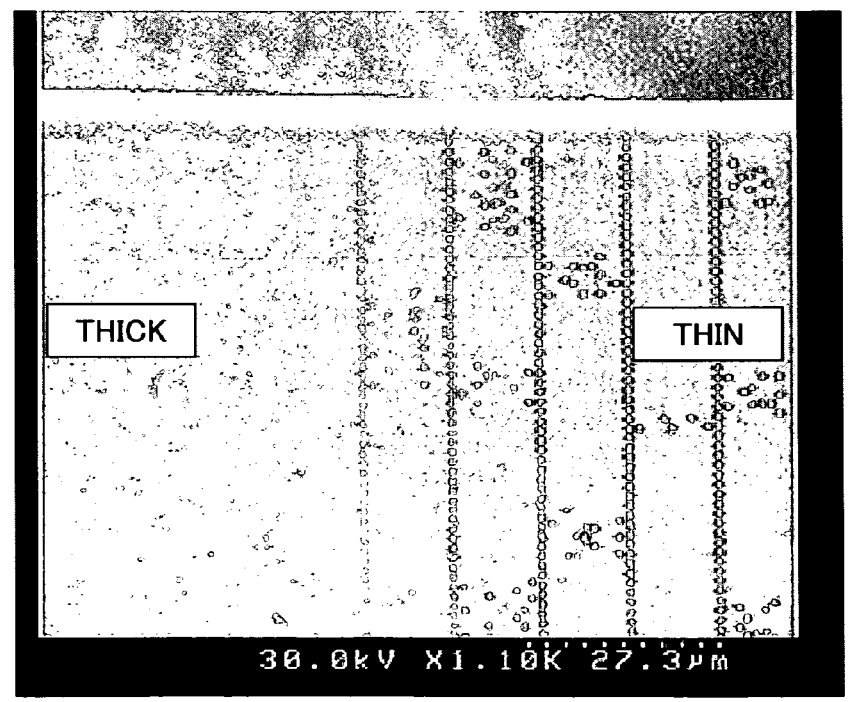

FIGS. 7A and 7B are images showing the pattern on the front side observed by using a SEM.

In FIGS. 7A and 7B, the thickness of the silicon substrate changes gradually from left to right. The silicon substrate is thicker in the left side than in the right side. FIGS. 7A and 7B are images showing the pattern on the front side observed from the backside by using a SEM at an accelerating voltage of 20 keV (7A) or 30 keV (7B), respectively. As the accelerating voltage increases, the thickness of the silicon substrate through which an electron can penetrate increases.

Figure 8:
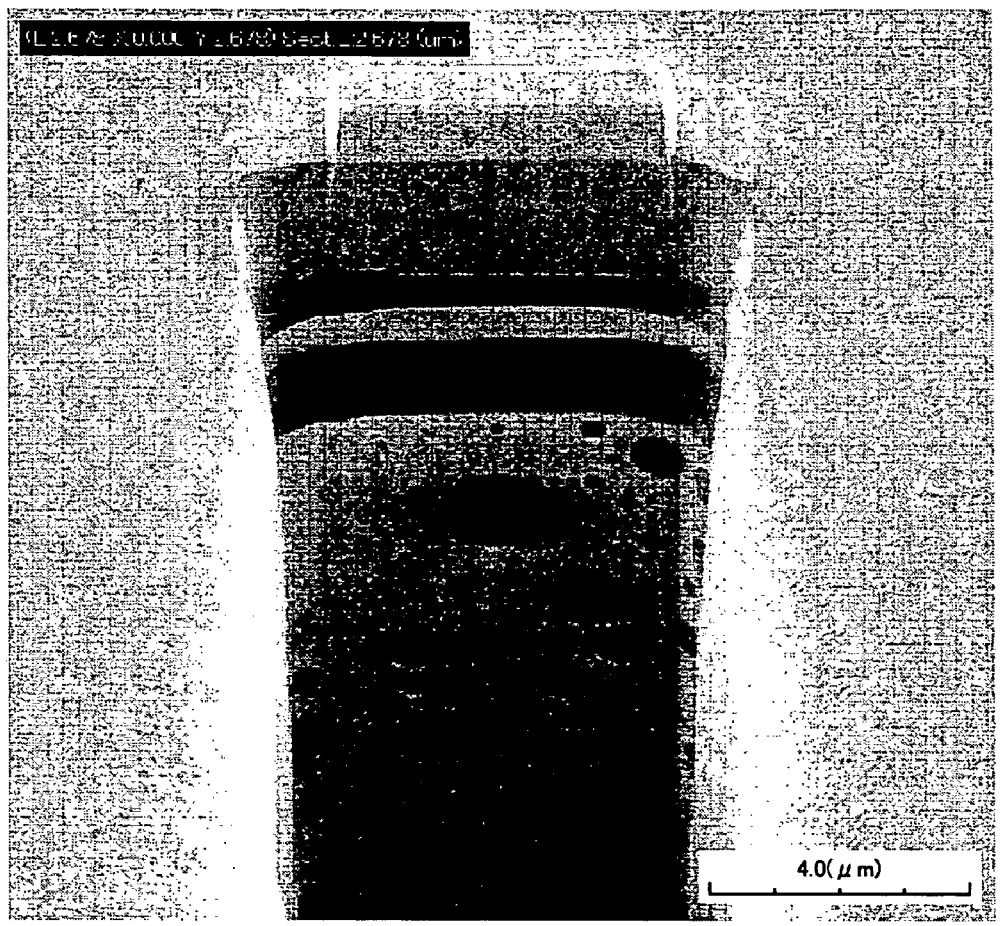
FIG. 8 is an image showing the remaining thickness of a silicon substrate measured by observing the cross section with a FIB.

FIG. 8 is an image showing the cross-sectional view of the silicon substrate observed by using a FIB. The measured thickness of the silicon substrate is approximately 3 µm. For this sample, interference fringes have been observed both by using a laser beam with a wavelength of 632.8 nm and by using an infrared ray with a wavelength of 1100 nm. Therefore, the thickness of the silicon substrate is measured to be less than 4.5 µm and the result conforms to the measurement result by a FIB.

In process 1-4, defect detection is performed again after reducing the thickness of the defect-containing area of the silicon substrate to 4 µm.

Figure 9:
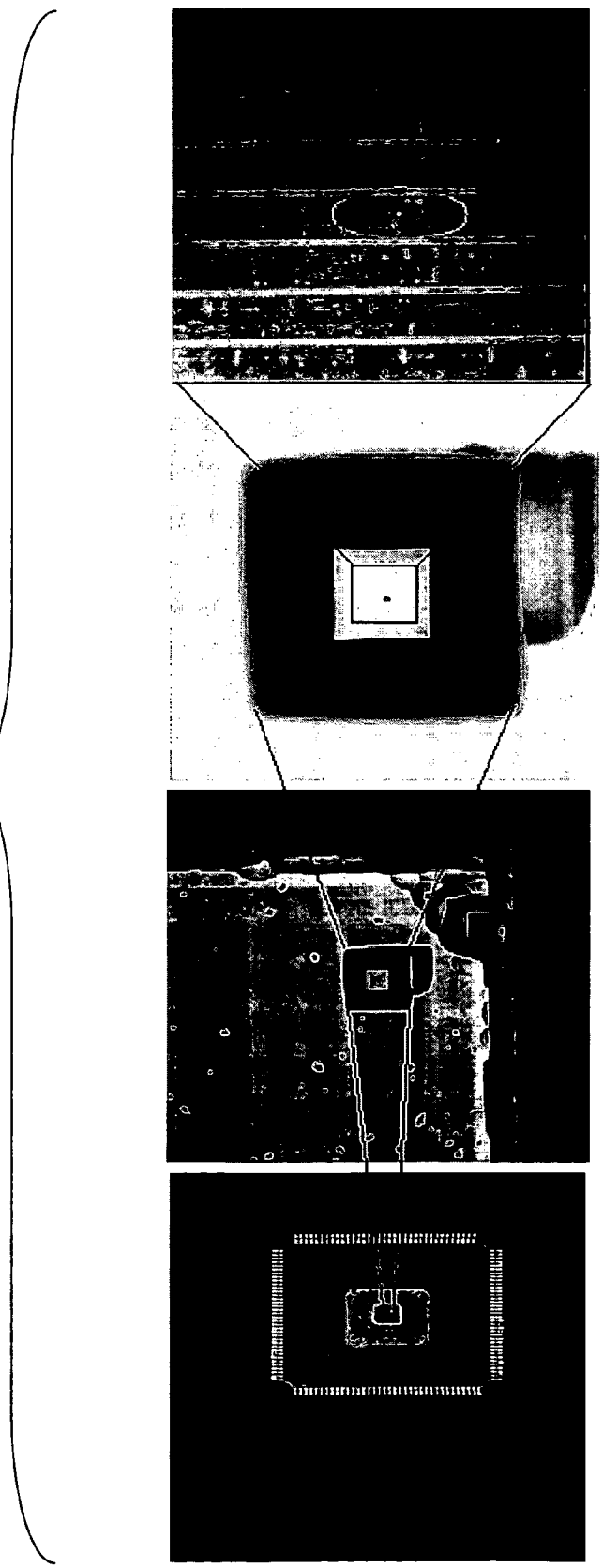
FIG. 9 is a collection of images showing the process which retries the detection of defects after the thickness of the defect-containing area of a silicon substrate is reduced to 4 μm, in which magnification increases from the bottom to the top.

The bottom image in FIG. 9 shows the entire backside of the device; the image second from the bottom shows an enlarged view of the area containing the defect-containing area; the image third from the bottom shows an enlarged view of the defect-containing area; and the top image is a further-enlarged view of the defect-containing area obtained by using an infrared microscope. Even when the thickness of the defect-containing area is reduced to 4 µm, since the defect-containing area is only a limited area of the silicon substrate, the mechanical strength of the silicon substrate is maintained. Also, since the metal layer is left intact, detection of electrical characteristics is still possible.

Again at this stage, defect detection is performed by using the PEMS technique.

In process 1-5, the location of the defect is marked.

The location of the defect is marked by using a laser beam so that the location can be easily identified when cutting out a sample for the TEM observation. For this marking, a laser in the PEMS apparatus or a laser in another apparatus may be used. When a laser in another apparatus is used, the same coordinate system should be used in both the PEMS apparatus and the other apparatus to determine the area to be processed. A laser beam with a fluence of 25 $J/cm^2$ is used for the marking and the depth of the mark is around 0.03 μm.

Figure 10A:
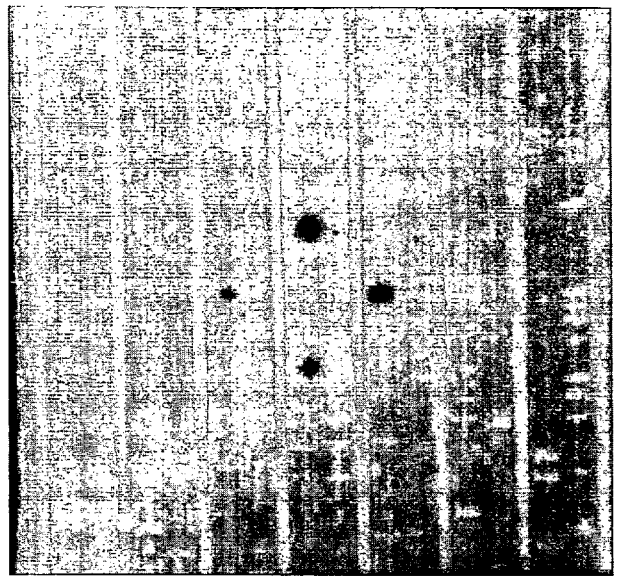
FIGS. 10A and 10B are images showing the marking correction process.
Figure 10B:
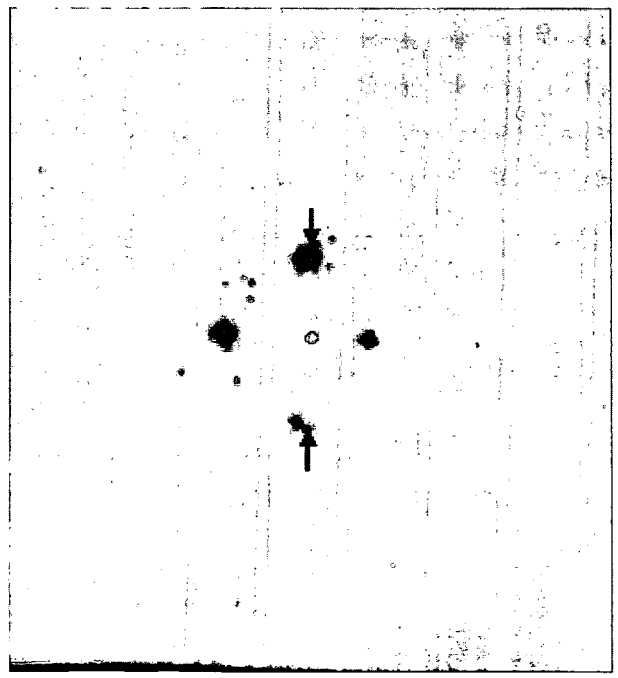

Since the mark is placed on the backside of the silicon substrate and the marking does not damage the front side metal layer, electrical defect detection is possible even after this process. If the newly identified location of the defect is not in the center of the mark marked in process 1-2, the position of the mark can be corrected at this stage. FIG. 10A shows the mark (four black points) formed in process 1-2 and FIG. 10B shows the corrected mark. The mark in FIG. 10B is corrected so that the defect is in the center of the four points.

In process 1-6, a sample for the TEM observation is cut out by using a FIB from the silicon substrate processed in processes 1 through 5. Although this process is not the main part of the first embodiment, the efficiency of the entire process can be improved by cutting out a sample using a FIB, just after the location of a defect is identified from the backside of the silicon substrate using processes 1 through 5. Since the area to be cut out is very thin, the accuracy of identifying the defect location is very high even from the backside and the processing time is not longer than the time required when this process is performed from the front side.

Figure 11:
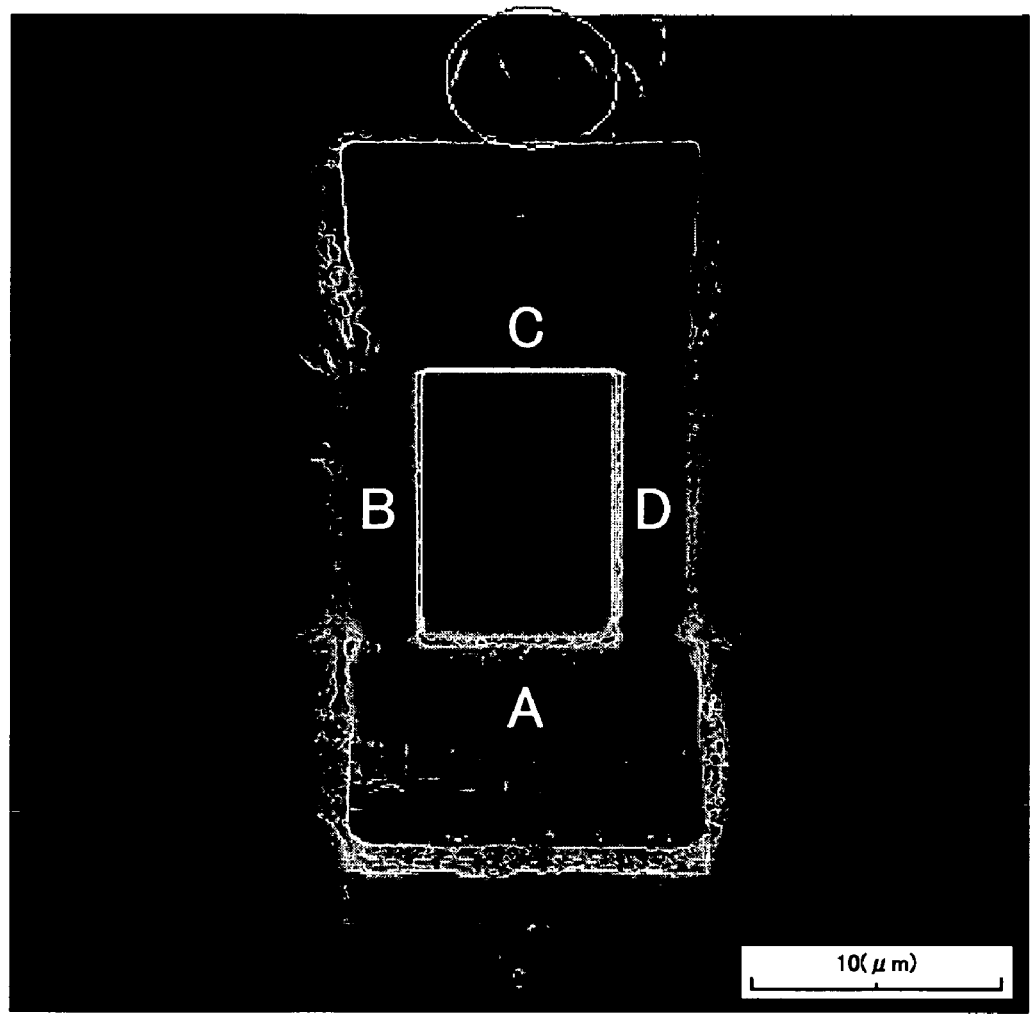
FIG. 11 is an image showing a part of the process which cuts out a sample used for the TEM observation.

In FIG. 11, a rectangular area of the silicon substrate is cut out. A thin slice of the defect-containing area which is parallel to the upper surface can be used as a sample for the plan-view TEM observation; a thin slice of the defect-containing area which is perpendicular to the upper surface can be used as a sample for the-cross-sectional TEM observation.

2. Second Embodiment

In the first embodiment, the PEMS technique is used for the defect detection. In the second embodiment, the OBIC technique is used for defect detection.

In the second embodiment, wet etching is performed on the backside of the silicon substrate as in the first embodiment until the thickness of the defect-containing area is reduced to 2 to 5 μm.

Figure 12:
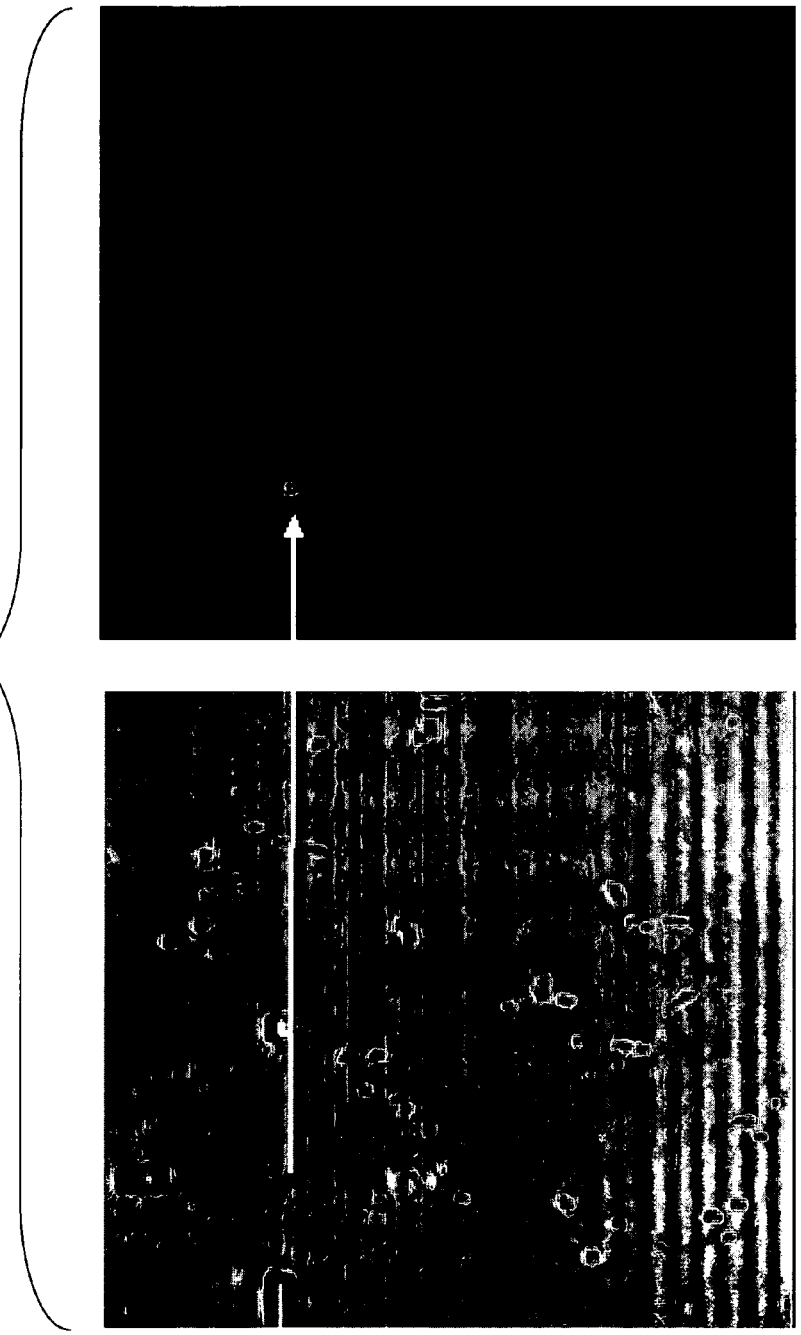
FIG. 12 is a collection of images in a second embodiment showing the OBIC observation from the backside.

After the above process, the silicon substrate is observed to detect defects from the backside using the OBIC technique. In FIG. 12, the lower image is a laser image showing the bottom of the defect-containing area and the upper image is an OBIC image from the backside. Since the defect-containing area is very thin, variations of the OBIC current can be observed from the backside. If a variation of the OBIC current is detected at this stage, the defect is a gate leakage or a junction leakage.

If no OBIC current variation is detected at this stage, it means there is no defect in the silicon substrate. Therefore, the remaining silicon substrate in the defect-containing area is removed by wet etching. For the wet etching, an alkaline solution used in the prior process is used. Since the remaining thickness of the defect-containing area of the silicon substrate is less than 5 μm, only a short time is needed to remove the remaining silicon substrate.

Figure 13:
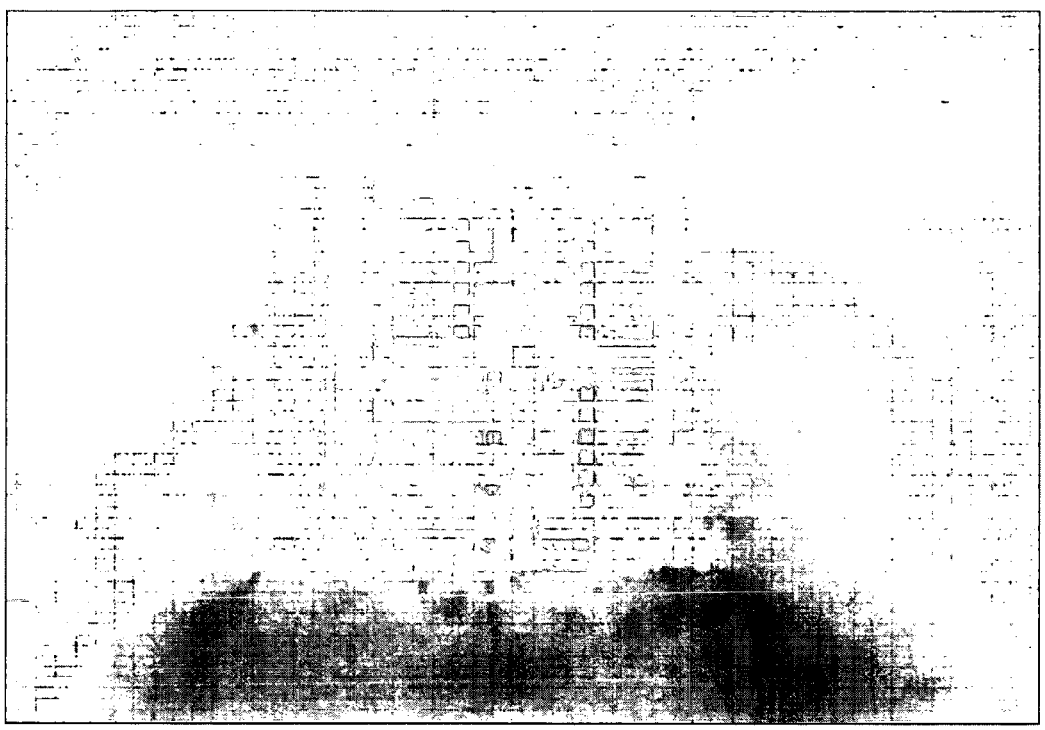
FIG. 13 is an optical microscope image in the second embodiment of the bottom of the defect-containing area where no silicon substrate remains.

FIG. 13 is an optical microscope image of the backside of the defect-containing area where no silicon substrate remains. The front side pattern can be observed from the backside of the defect-containing area. At this stage, the OBIRCH observation is performed. If a variation of the OBIRCH current is observed, it means that there is a defect is the metal layer and the defect is considered to be a high resistance or open/short circuit in the metal layer.

If a defect is detected by the OBIRCH observation, the location is marked on the backside of the silicon substrate by using a laser beam.

3. Third Embodiment

In the third embodiment, a sample for the plan-view TEM is created by cutting out a part of the defect-containing area from the silicon substrate in which the location of a defect is identified using a method described in the first or second embodiment.

In process 3-1, a silicon substrate is processed using a method according to an embodiment of the present invention. The remaining thickness of the backside of the defect-containing area of the silicon substrate is assumed to be 4 μm.

In process 3-2, a protective carbon film is deposited on the backside and the defect-containing area of the silicon substrate is cut out by using a FIB from the backside of the silicon substrate. The thickness of the protective carbon film is around 1 μm. The deposited carbon protective film protects necessary parts from the FIB. Also, since the carbon protective film is conductive, the film prevents charge-up.

Figure 14A:
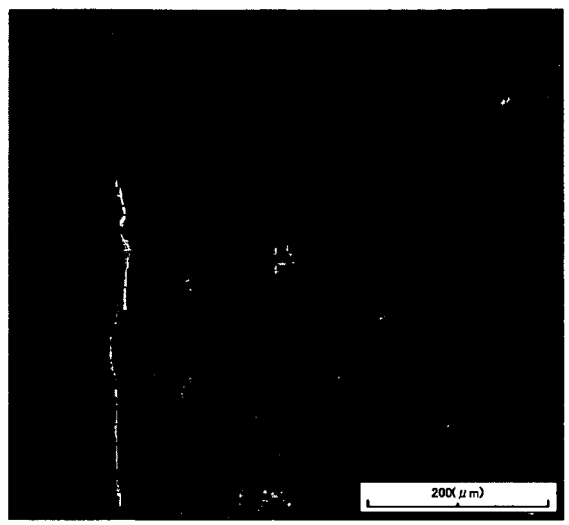
FIGS. 14A through 14C are images showing the first half of the process in a third embodiment which process cuts out a defect-containing area from a defect-containing silicon substrate to create a sample for the plan-view TEM.
Figure 14B:
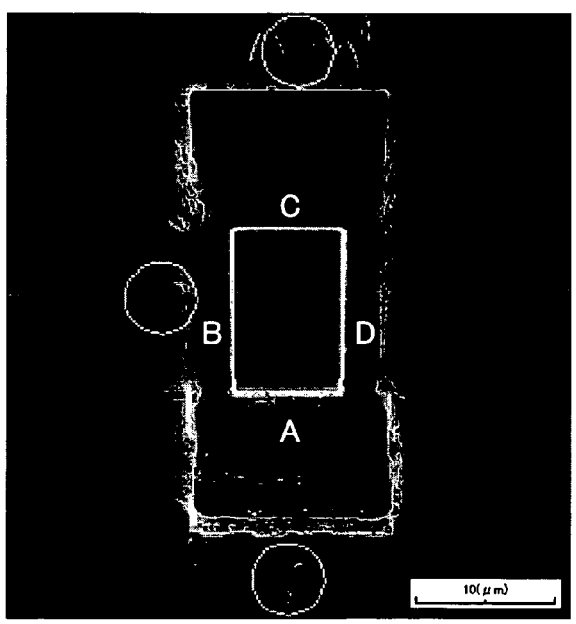
Figure 14C:
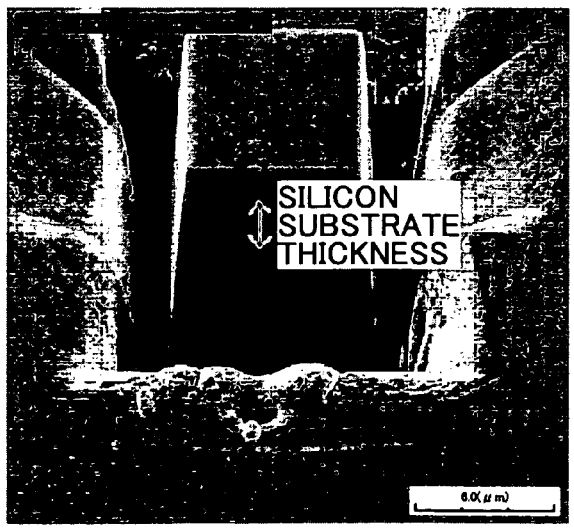

The size of the defect-containing area may be approximately 10 μm×10 μm×10 μm. The area to be cut out is determined based on the mark indicating the location of the defect. The defect should be contained in the center of the cube. FIG. 14A shows the defect-containing area and FIG. 14B is a magnified image of FIG. 14A. In FIG. 14B, the cube is seen from above and four sides of the upper surface are indicated by symbols A, B, C, and D. The lateral faces that correspond to those four sides are called faces A, B, C, and D. The sample to be finally cut out for the TEM observation may be a thin slice with a thickness of 0.1 to 0.4 μm which is parallel to the upper surface. Face C should be finished carefully so that the face can be used to determine the position for the sample. FIG. 14C shows an image seen from direction C. Circles in FIG. 14B show the points marked to indicate the defect location. At this stage, the base part of the defect-containing area is still connected to the silicon substrate.

In process 3-3, after face C is finished, the base part of the defect-containing area is cut off by irradiating side A with an ion beam at a 45-degree angle. Face C is not irradiated with an ion beam. With the ion beam irradiation, the defect-containing area is cut off from the silicon substrate and falls in direction A in the hole formed by the groove created when the area is cut out.

Figure 15A:
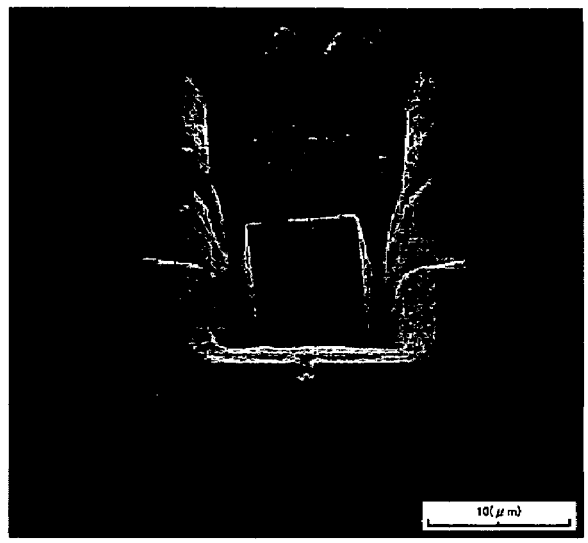
FIGS. 15A through 15C are images in which the base part of the defect-containing area is cut off by irradiating side A with an ion beam and the defect-containing area falls in direction A.
Figure 15B:
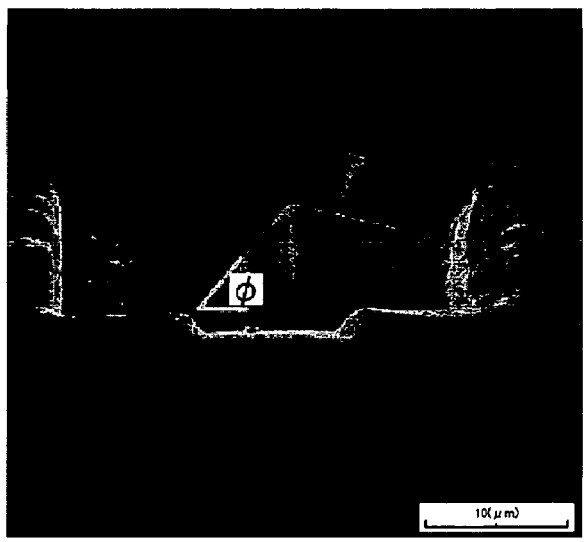
Figure 15C:
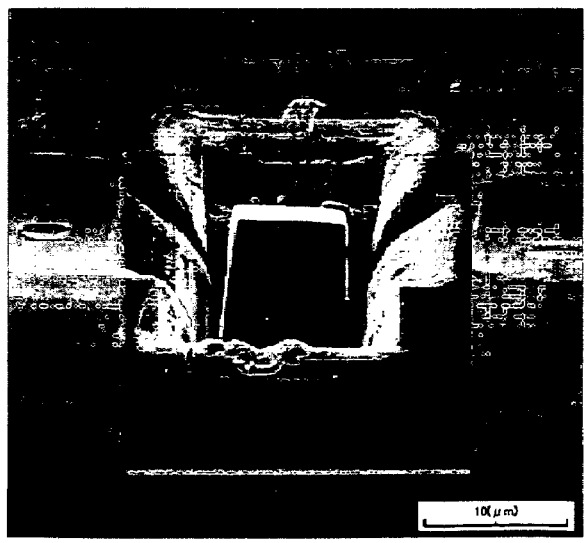

FIGS. 15A through 15C are images in which the base part of the defect-containing area is cut off by irradiating side A with an ion beam and the defect-containing area falls in direction A. FIG. 15A is an image seen from direction A, 15B is an image seen from direction B, and 15C is an image seen from direction C. In FIG. 15B, the angle of falling φ is 45 to 60 degrees. In FIG. 15C, face C used to determine the position of the sample is facing obliquely upward.

Figure 16:
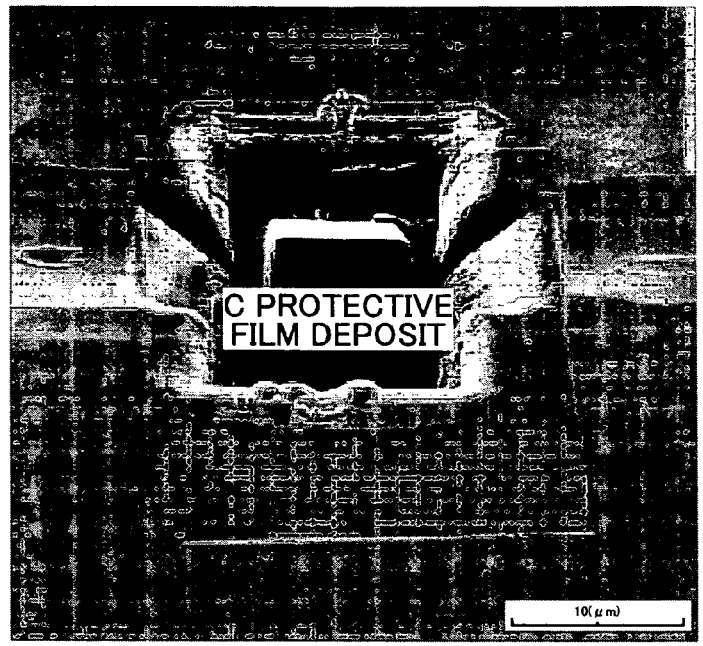
FIG. 16 is an image in which a protective carbon film is deposited from direction C.

In process 3-4, the silicon substrate is tilted about 45-degrees so that face C faces upward. Then, a protective carbon film is selectively deposited on an area covering the defect-containing area on face C and the silicon substrate to fix the area in the hole to the silicon substrate. In this selective deposition process, the FIB apparatus is fed with a carbon containing gas, the target area is irradiated with the FIB, and carbon is deposited on the area. FIG. 16 is an image in which a protective carbon film is deposited.

Figure 17:
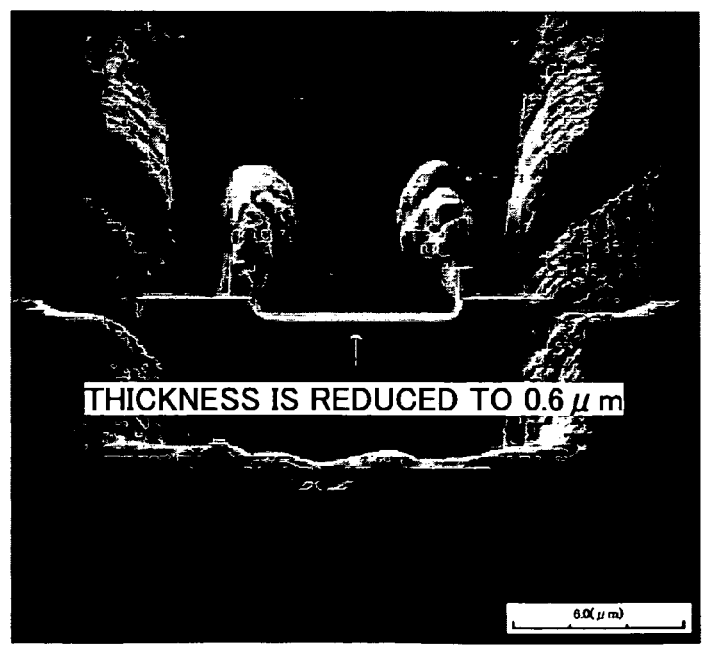
FIG. 17 is an image in which the defect-containing area is processed to form a thin slice having a thickness of 0.6 μm and containing a defect in the center.
Figure 18:
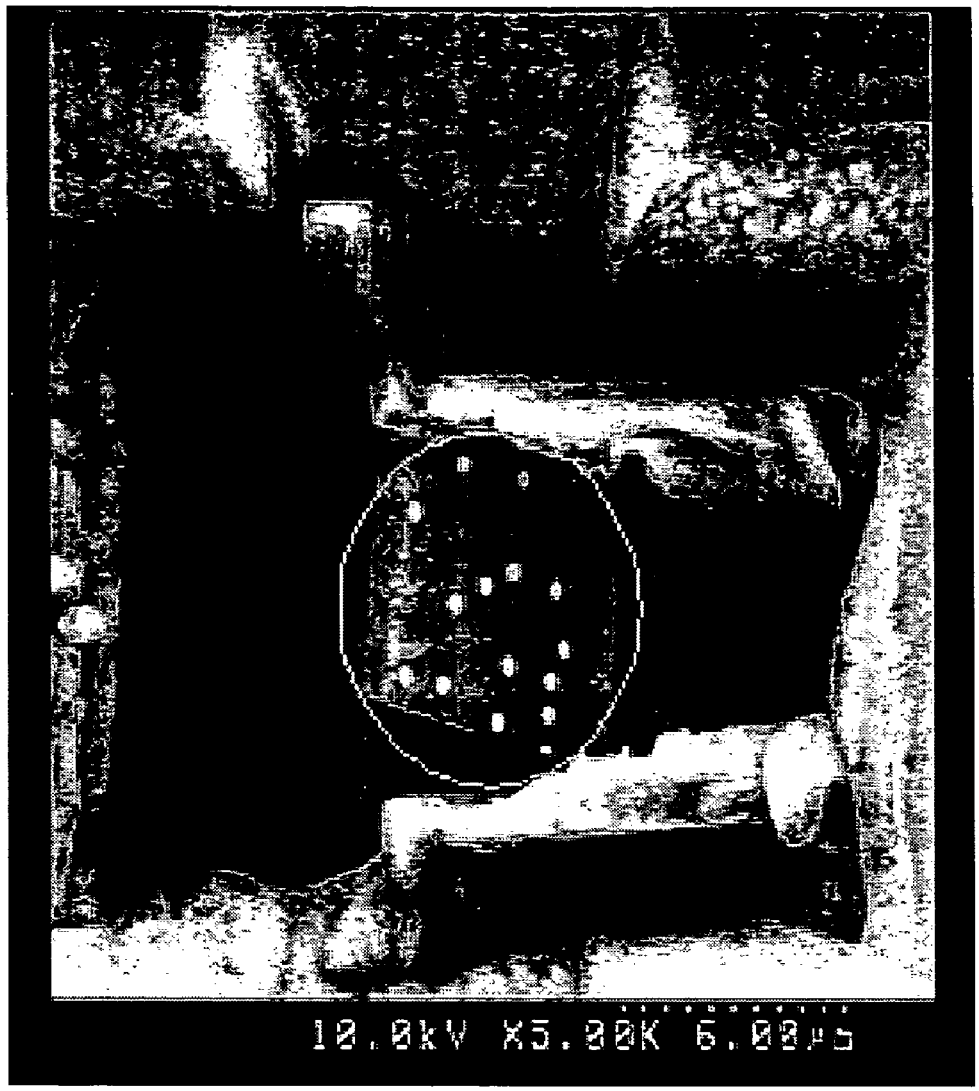
FIG. 18 is an image in which the thickness of the thin slice is further reduced so that the slice can be used as a sample for the plan-view TEM observation.

As shown in FIGS. 17 and 18, the fallen defect-containing area which is fixed in the hole by the protective carbon film is processed to create a thin slice used as a sample for the TEM observation. FIG. 17 is an image in which the defect-containing area is processed by irradiating face C at a right angle with the FIB to form a thin slice having a thickness of 0.6 μm and containing a defect in the center.

The thickness of the thin slice is further reduced to 0.1 to 0.4 μm by using the FIB. Finally, two sides and the bottom of the thin slice are cut off by using the FIB to create a sample for the plan-view TEM observation.

The created sample is taken out by using a pickup technique and placed in a TEM apparatus for observation.

In the following, embodiments of the present invention are summarized.

The methods according to an embodiment of the present invention may be used to process a silicon substrate of a failed semiconductor integrated circuit device, to detect a defect in the silicon substrate, and to create a sample for the TEM observation.

A silicon substrate processing method according to an embodiment of the present invention for reducing the thickness of an area of a silicon substrate on which a metal layer is formed to implement a semiconductor integrated circuit includes: (A) a process which evenly reduces the thickness of the backside of a silicon substrate to an extent where mechanical strength is maintained and the metal layer on the silicon substrate remains intact; (B) a process which detects defects from a backside of the silicon substrate after the process (A); (C) a process which further reduces the thickness of a defect-containing area of the silicon substrate by processing the backside of the silicon substrate; (D) a process which measures the thickness of the area of the silicon substrate which is reduced in the process (C), including at least a step that measures the thickness of the silicon substrate based on interference fringes formed by irradiating the substrate from the backside with a light.

In an embodiment of the present invention, since the backside of the silicon substrate is processed with the metal layer on the silicon substrate remaining intact, techniques which incorporate detection of electrical characteristics can be used in the process (B) for detecting defects.

Such techniques which incorporate detection of electrical characteristics may include an OBIC technique, an OBIRCH technique, and a PEMS technique.

The process (C) for reducing the thickness may include a step which etches the silicon substrate using a laser beam to form a concave area and a subsequent step which performs anisotropic wet etching using an alkaline solution.

The process (D) for measuring the thickness of the defect-containing area of the silicon substrate may include a step which measures the thickness of the defect-containing area of the silicon substrate using an infrared ray before interference fringes appear.

The measurement step using an infrared ray may be implemented so that the thickness is measured based on either a distance between focal points obtained by focusing an infrared microscope on the front side and backside of the defect-containing area of the silicon substrate, or the intensity of an infrared ray which penetrates through the defect-containing area of the silicon substrate. At this stage, the thickness measurement may not be of high accuracy. The measurement method using an infrared ray can measure a thickness of 10 μm or more.

For the thickness measurement based on interference fringes in the process (D), the use of a laser beam is preferable. The range of the thickness which can be measured based on interference fringes depends on the wavelength and intensity of the laser beam. When a single laser beam is used, the thickness of the defect-containing area of the silicon substrate is measured to be less than the thickness determined by observation of interference fringes formed by the wavelength. When two laser beams with different wavelengths are used, the thickness of the defect-containing area of the silicon substrate is measured to be in a range between thicknesses determined by the two wavelengths.

The process (D) may include a step which measures the thickness of the defect-containing area of the silicon substrate based on interference fringe formation and electron acceleration energy which is detected when the pattern on the front side of the defect-containing area is observed from the backside of the silicon substrate using a scanning electron microscope (SEM). As the electron acceleration energy becomes stronger, an electron beam can penetrate a thicker silicon substrate. Therefore, the electron acceleration energy detected when the front side pattern is observed corresponds to the thickness of the silicon substrate.

It is preferable to alternately repeat the anisotropic wet etching in the process (C) and the thickness measurement in the process (D) until interference fringes appear, and even until the pattern on the front side can be observed by using the SEM.

Even after the interference fringes appear, the anisotropic wet etching may be continued for a specific period of time so that a desired thickness is achieved for the defect-containing area of the silicon substrate.

In the thickness-reducing process (C), as an alkaline solution used for the anisotropic wet etching performed after the etching step using a laser beam, a potassium hydroxide (KOH) solution, a tetramethylammonium hydroxide (TMAH) solution, an ethylenediamine pyrocatechol (EDP) solution, a sodium hydroxide (NaOH) solution, or an ammonia ($NH_4OH$) solution may be used.

As the laser beam, a short-wavelength laser beam for which the absorption coefficient of silicon is large is preferable. A short-wavelength laser beam is absorbed by the silicon substrate before reaching a metal layer on the front side and will not damage the metal layer.

A defect-detecting method according to the present invention includes: a process which processes a silicon substrate to achieve a thickness that enables appearance of light interference fringes, is greater than a depth of diffusion layers formed on the front side of the silicon substrate, and allows a visible laser beam to reach the diffusion layers from the backside of the silicon substrate; and a subsequent process which identifies locations of defects.

Two most common defects in a silicon substrate are PN junction leakage and gate oxide leakage.

One technique to detect defects in a silicon substrate is an OBIC technique which detects defects from the backside of the silicon substrate.

Another technique to detect defects in a silicon substrate is a PEMS technique which detects defects from the backside of the silicon substrate.

To detect a PN junction leakage or a gate oxide leakage and to identify a specific location of a defect, a suitable thickness of a defect-containing area of a silicon substrate is 2 to 5 μm.

The process for detecting defects in a silicon substrate may preferably include a step which, if no defect is detected, performs anisotropic wet etching until no silicon substrate remains in the defect-containing area, and then identifies locations of defects in the metal layer formed on the front side of the silicon substrate.

The two most common defects in metal layers are an open/short circuit and high resistance in the metal layer.

An OBIRCH technique which detects defects from the backside of a silicon substrate is used to detect defects in a metal layer.

The present invention enables a defect-detecting method using a single apparatus in which the OBIC technique is used to detect defects in a silicon substrate, the OBIRCH technique is used to detect defects in a metal layer, and a visible laser beam is used in both techniques.

The present application is based on Japanese Priority Application No. 2005-139518, filed on May 12, 2005, the entire contents of which are hereby incorporated herein by reference.

What is claimed is:

1. A silicon substrate processing method which reduces thickness of an area of a silicon substrate on which a metal layer is formed to implement a semiconductor integrated circuit, comprising the steps of:
   (A) evenly reducing thickness of a backside of the silicon substrate to an extent where mechanical strength is maintained and the metal layer on the silicon substrate remains intact;
   (B) detecting a defect from the backside of the silicon substrate after the step (A);
   (C) further reducing the thickness of an area of the silicon substrate containing the defect by processing the backside of the silicon substrate;
   (D) measuring the thickness of the defect-containing area of the silicon substrate which is reduced in the step (C), and determining whether interference fringes are formed by irradiating the silicon substrate from the backside with a light, and if interferences are not formed, repeating steps (C) and (D),
   wherein the step (D) of measuring the thickness of the defect-containing area of the silicon substrate includes a step which measures the thickness based on the interference fringe formation and electron acceleration energy which is detected when a pattern on a front side of the defect-containing area is observed from the backside of the silicon substrate by using a SEM.

2. The silicon substrate processing method as claimed in claim 1, wherein a technique which incorporates detection of electrical characteristics is used in the step (B) of detecting a defect.

3. The silicon substrate processing method as claimed in claim 2, wherein the defect-detecting technique is an OBIC technique, an OBIRCH technique, or a PEMS technique.

4. The silicon substrate processing method as claimed in claim 1, wherein the step (C) of reducing the thickness includes:
   a step of etching the silicon substrate using a laser beam; and
   a subsequent step of performing anisotropic wet etching using an alkaline solution.

5. The silicon substrate processing method as claimed in claim 4, wherein the anisotropic wet etching in the step (C) and the thickness measurement in the step (D) are repeated alternately until the interference fringes appear or until the pattern on the front side of the defect-containing area can be observed by using the SEM.

6. The silicon substrate processing method as claimed in claim 4, wherein the anisotropic wet etching is continued for a specific period of time even after the interference fringes appear, so that a desired thickness is achieved for the defect-containing area of the silicon substrate.

7. The silicon substrate processing method as claimed in claim 4, wherein a short-wavelength laser beam for which an absorption coefficient of silicon is large is used as the laser beam.

8. The silicon substrate processing method as claimed in claim 4, wherein a KOH solution, a TMAH solution, an EDP solution, a NaOH solution, or a $NH_4OH$ solution is used as the alkaline solution.

9. The silicon substrate processing method as claimed in claim 1,
   wherein the step (D) of measuring the thickness of the defect-containing area of the silicon substrate includes a step of measuring the thickness of the defect-containing area of the silicon substrate using an infrared ray before the interference fringes appear.

10. The silicon substrate processing method us claimed in claim 9, wherein the measurement step using an infrared ray is implemented so that the thickness is measured based on either a distance between focal points obtained by focusing an infrared microscope on both sides of the defect-containing area of the silicon substrate, or intensity of an infrared ray which penetrates through the defect-containing area of the silicon substrate.

11. The silicon substrate processing method as claimed in claim 1, wherein laser beams with different wavelengths are used in the step (D) of measuring the thickness based on the interference fringes.

12. A defect-detecting method comprising the steps of:
   (I) processing a silicon substrate using a method including the following steps (A) through (D) to achieve a thickness that enables appearance of light interference fringes in a defect-containing area, the thickness of the processed silicon substrate being greater than a depth of diffusion layers formed on a front side of the silicon substrate, and allowing a visible laser beam to reach the diffusion layers from a backside of the silicon substrate;
      (A) evenly reducing thickness of a backside of the silicon substrate to an extent where mechanical strength is maintained and the metal layer on the silicon substrate remains intact;
      (B) detecting a defect from the backside of the silicon substrate after the step (A);
      (C) further reducing the thickness of an area of the silicon substrate containing the defect by processing the backside of the silicon substrate;
      (D) measuring the thickness of the defect-containing area of the silicon substrate which is reduced in the step (C), and determining whether interference fringes are formed by irradiating the silicon substrate from the backside with a light, and if interferences are not formed, repeating steps (C) and (D), wherein the step (D) includes a step of measuring the thickness of the defect-containing area of the silicon substrate based on interference fringe formation and electron acceleration energy which is detected when a pattern on a front side of the defect-containing area is observed from the backside of the silicon substrate by using a SEM;
   (II) detecting a defect in the silicon substrate; and
   (III) placing on the backside of the silicon substrate a mark showing the defect location.

13. The defect-detecting method as claimed in claim 12, wherein an OBIC technique is used to detect a defect in the silicon substrate from the backside of the silicon substrate.

14. The defect-detecting method as claimed in claim 12, wherein a PEMS technique is used to detect a defect in the silicon substrate from the backside of the silicon substrate.

15. The defect-detecting method as claimed in claim 12, wherein remaining thickness of the defect-containing area of the silicon substrate is 2 to 5 μm.

16. The defect-detecting method as claimed in claim 12, further comprising the step of:
   correcting a position of the mark after performing defect detection again.

17. The defect-detecting method as claimed in claim 12, further comprising the steps of:
   performing anisotropic wet etching, if no defect is detected in step (II), until no silicon substrate is left in the defect-containing area; and
   detecting a defect in a metal layer formed on the front side of the silicon substrate.

18. The defect-detecting method as claimed in claim 17, wherein an OBIRCH technique is used to detect a defect in the metal layer from the backside or the front side of the silicon substrate.

19. The defect-detecting method as claimed in claim 18, wherein a single apparatus is used for defect detection, in which the OBIC technique is used to detect a defect in the silicon substrate, the OBIRCH technique is used to detect a defect in the metal layer, and a visible laser beam is used in both techniques.

* * * * *